US010532174B2

(12) United States Patent
Al-Ali

(10) Patent No.: US 10,532,174 B2
(45) Date of Patent: Jan. 14, 2020

(54) ASSISTIVE CAPNOGRAPHY DEVICE

(71) Applicant: MASIMO CORPORATION, Irvine, CA (US)

(72) Inventor: Ammar Al-Ali, San Juan Capistrano, CA (US)

(73) Assignee: MASIMO CORPORATION, Irvine, CA (US)

( * ) Notice: Subject to any disclaimer, the term of this patent is extended or adjusted under 35 U.S.C. 154(b) by 989 days.

(21) Appl. No.: 14/627,500

(22) Filed: Feb. 20, 2015

(65) Prior Publication Data

US 2015/0238722 A1    Aug. 27, 2015

Related U.S. Application Data

(60) Provisional application No. 61/943,263, filed on Feb. 21, 2014.

(51) Int. Cl.
    *A61M 16/00*    (2006.01)
    *A61M 16/10*    (2006.01)
    (Continued)

(52) U.S. Cl.
    CPC ....... *A61M 16/1005* (2014.02); *A61B 5/0836* (2013.01); *A61M 16/0051* (2013.01); *A61M 16/0084* (2014.02); *A61M 16/085* (2014.02); *A61B 5/082* (2013.01); *A61B 5/097* (2013.01); *A61B 5/4836* (2013.01); *A61B 5/7445* (2013.01); *A61B 2505/01* (2013.01); *A61B 2560/0443* (2013.01); *A61M 16/0003* (2014.02);
    (Continued)

(58) Field of Classification Search
    CPC ........ A61M 16/00; A61M 16/06–0694; A61M 16/20–209; A61M 16/003–0012; A61M 16/0078; A61M 16/0084; A61M 2016/0015–0042; A62B 9/00; A62B 9/02–027; A62B 7/00; A62B 7/14; A62B 2205/502; B63C 11/12; B63C 11/18
    See application file for complete search history.

(56) References Cited

U.S. PATENT DOCUMENTS 3,046,978 A * 7/1962 Lea ................. A61M 16/00
                                                128/205.13
4,919,132 A * 4/1990 Miser .............. A61M 16/00
                                                116/277
(Continued)

OTHER PUBLICATIONS

US 8,845,543 B2, 09/2014, Diab et al. (withdrawn)

*Primary Examiner* — Tan-Uyen T Ho
*Assistant Examiner* — Ned T Heffner
(74) *Attorney, Agent, or Firm* — Knobbe Martens Olson & Bear, LLP

(57) ABSTRACT

Systems and method for monitoring patient physiological data are presented herein. A gas analyzing measurement head can be provided to sample and analyze respiratory gases of a patient. In one embodiment, the gas analyzing measurement head can read information on an information element of an airway adapter or resuscitation bag. Such information can be used to generate instructions for manual ventilation using the gas analyzing measurement head, airway adapter, and resuscitation bag. Manual ventilation instructions can be displayed on the gas analyzing measurement head or can be transmitted for display on another device, such as a clinician's mobile computing device.

19 Claims, 12 Drawing Sheets

(51) Int. Cl.
*A61M 16/08* (2006.01)
*A61B 5/083* (2006.01)
*A61M 16/04* (2006.01)
*A61M 16/06* (2006.01)
*A61M 16/20* (2006.01)
*A61M 16/01* (2006.01)
*A61B 5/00* (2006.01)
*A61B 5/08* (2006.01)
*A61B 5/097* (2006.01)

(52) U.S. Cl.
CPC ............ *A61M 16/01* (2013.01); *A61M 16/04* (2013.01); *A61M 16/06* (2013.01); *A61M 16/208* (2013.01); *A61M 2016/103* (2013.01); *A61M 2205/35* (2013.01); *A61M 2205/505* (2013.01); *A61M 2230/432* (2013.01)

(56) References Cited

U.S. PATENT DOCUMENTS

| | | | |
|---|---|---|---|
| 4,960,128 | A | 10/1990 | Gordon et al. |
| 4,964,408 | A | 10/1990 | Hink et al. |
| 5,041,187 | A | 8/1991 | Hink et al. |
| 5,069,213 | A | 12/1991 | Polczynski |
| 5,163,438 | A | 11/1992 | Gordon et al. |
| 5,319,355 | A | 6/1994 | Russek |
| 5,337,744 | A | 8/1994 | Branigan |
| 5,341,805 | A | 8/1994 | Stavridi et al. |
| D353,195 | S | 12/1994 | Savage et al. |
| D353,196 | S | 12/1994 | Savage et al. |
| 5,377,676 | A | 1/1995 | Vari et al. |
| D359,546 | S | 6/1995 | Savage et al. |
| 5,431,170 | A | 7/1995 | Mathews |
| D361,840 | S | 8/1995 | Savage et al. |
| D362,063 | S | 9/1995 | Savage et al. |
| 5,452,717 | A | 9/1995 | Branigan et al. |
| D363,120 | S | 10/1995 | Savage et al. |
| 5,456,252 | A | 10/1995 | Vari et al. |
| 5,479,934 | A | 1/1996 | Imran |
| 5,482,036 | A | 1/1996 | Diab et al. |
| 5,490,505 | A | 2/1996 | Diab et al. |
| 5,494,043 | A | 2/1996 | O'Sullivan et al. |
| 5,533,511 | A | 7/1996 | Kaspari et al. |
| 5,534,851 | A | 7/1996 | Russek |
| 5,561,275 | A | 10/1996 | Savage et al. |
| 5,562,002 | A | 10/1996 | Lalin |
| 5,590,649 | A | 1/1997 | Caro et al. |
| 5,591,130 | A * | 1/1997 | Denton ............ A61M 16/0078 128/202.22 |
| 5,602,924 | A | 2/1997 | Durand et al. |
| 5,620,004 | A * | 4/1997 | Johansen ............ A61B 7/003 600/529 |
| 5,632,272 | A | 5/1997 | Diab et al. |
| 5,638,816 | A | 6/1997 | Kiani-Azarbayjany et al. |
| 5,638,818 | A | 6/1997 | Diab et al. |
| 5,645,440 | A | 7/1997 | Tobler et al. |
| 5,685,299 | A | 11/1997 | Diab et al. |
| 393,830 | | 4/1998 | Tobler et al. |
| 5,743,262 | A | 4/1998 | Lepper, Jr. et al. |
| 5,758,644 | A | 6/1998 | Diab et al. |
| 5,760,910 | A | 6/1998 | Lepper, Jr. et al. |
| 5,769,785 | A | 6/1998 | Diab et al. |
| 5,782,757 | A | 7/1998 | Diab et al. |
| 5,785,659 | A | 7/1998 | Caro et al. |
| 5,791,347 | A | 8/1998 | Flaherty et al. |
| 5,810,734 | A | 9/1998 | Caro et al. |
| 5,823,950 | A | 10/1998 | Diab et al. |
| 5,830,131 | A | 11/1998 | Caro et al. |
| 5,833,618 | A | 11/1998 | Caro et al. |
| 5,860,919 | A | 1/1999 | Kiani-Azarbayjany et al. |
| 5,890,929 | A | 4/1999 | Mills et al. |
| 5,904,654 | A | 5/1999 | Wohltmann et al. |
| 5,919,134 | A | 7/1999 | Diab |
| 5,934,925 | A | 8/1999 | Tobler et al. |
| 5,940,182 | A | 8/1999 | Lepper, Jr. et al. |
| 5,957,127 | A * | 9/1999 | Yamamori ............ A61B 5/0836 128/204.22 |
| 5,995,855 | A | 11/1999 | Kiani et al. |
| 5,997,343 | A | 12/1999 | Mills et al. |
| 6,002,952 | A | 12/1999 | Diab et al. |
| 6,011,986 | A | 1/2000 | Diab et al. |
| 6,027,452 | A | 2/2000 | Flaherty et al. |
| 6,036,642 | A | 3/2000 | Diab et al. |
| 6,045,509 | A | 4/2000 | Caro et al. |
| 6,067,462 | A | 5/2000 | Diab et al. |
| 6,081,735 | A | 6/2000 | Diab et al. |
| 6,088,607 | A | 7/2000 | Diab et al. |
| 6,110,522 | A | 8/2000 | Lepper, Jr. et al. |
| 6,124,597 | A | 9/2000 | Shehada |
| 6,128,521 | A | 10/2000 | Marro et al. |
| 6,129,675 | A | 10/2000 | Jay |
| 6,144,868 | A | 11/2000 | Parker |
| 6,151,516 | A | 11/2000 | Kiani-Azarbayjany et al. |
| 6,152,754 | A | 11/2000 | Gerhardt et al. |
| 6,157,850 | A | 12/2000 | Diab et al. |
| 6,165,005 | A | 12/2000 | Mills et al. |
| 6,184,521 | B1 | 2/2001 | Coffin, IV et al. |
| 6,206,830 | B1 | 3/2001 | Diab et al. |
| 6,229,856 | B1 | 5/2001 | Diab et al. |
| 6,232,609 | B1 | 5/2001 | Snyder et al. |
| 6,236,872 | B1 | 5/2001 | Diab et al. |
| 6,241,683 | B1 | 6/2001 | Macklem et al. |
| 6,253,097 | B1 | 6/2001 | Aronow et al. |
| 6,256,523 | B1 | 7/2001 | Diab et al. |
| 6,263,222 | B1 | 7/2001 | Diab et al. |
| 6,278,522 | B1 | 8/2001 | Lepper, Jr. et al. |
| 6,280,213 | B1 | 8/2001 | Tobler et al. |
| 6,285,896 | B1 | 9/2001 | Tobler et al. |
| 6,301,493 | B1 | 10/2001 | Marro et al. |
| 6,317,627 | B1 | 11/2001 | Ennen et al. |
| 6,321,100 | B1 | 11/2001 | Parker |
| 6,325,761 | B1 | 12/2001 | Jay |
| 6,334,065 | B1 | 12/2001 | Al-Ali et al. |
| 6,343,224 | B1 | 1/2002 | Parker |
| 6,349,228 | B1 | 2/2002 | Kiani et al. |
| 6,360,114 | B1 | 3/2002 | Diab et al. |
| 6,368,283 | B1 | 4/2002 | Xu et al. |
| 6,371,921 | B1 | 4/2002 | Caro et al. |
| 6,377,829 | B1 | 4/2002 | Al-Ali |
| 6,388,240 | B2 | 5/2002 | Schulz et al. |
| 6,397,091 | B2 | 5/2002 | Diab et al. |
| 6,430,437 | B1 | 8/2002 | Marro |
| 6,430,525 | B1 | 8/2002 | Weber et al. |
| 6,463,311 | B1 | 10/2002 | Diab |
| 6,470,199 | B1 | 10/2002 | Kopotic et al. |
| 6,501,975 | B2 | 12/2002 | Diab et al. |
| 6,505,059 | B1 | 1/2003 | Kollias et al. |
| 6,515,273 | B2 | 2/2003 | Al-Ali |
| 6,519,487 | B1 | 2/2003 | Parker |
| 6,525,386 | B1 | 2/2003 | Mills et al. |
| 6,526,300 | B1 | 2/2003 | Kiani et al. |
| 6,541,756 | B2 | 4/2003 | Schulz et al. |
| 6,542,764 | B1 | 4/2003 | Al-Ali et al. |
| 6,580,086 | B1 | 6/2003 | Schulz et al. |
| 6,584,336 | B1 | 6/2003 | Ali et al. |
| 6,595,316 | B2 | 7/2003 | Cybulski et al. |
| 6,597,932 | B2 | 7/2003 | Tian et al. |
| 6,597,933 | B2 | 7/2003 | Kiani et al. |
| 6,606,511 | B1 | 8/2003 | Ali et al. |
| 6,632,181 | B2 | 10/2003 | Flaherty et al. |
| 6,639,668 | B1 | 10/2003 | Trepagnier |
| 6,640,116 | B2 | 10/2003 | Diab |
| 6,643,530 | B2 | 11/2003 | Diab et al. |
| 6,650,917 | B2 | 11/2003 | Diab et al. |
| 6,654,624 | B2 | 11/2003 | Diab et al. |
| 6,658,276 | B2 | 12/2003 | Kiani et al. |
| 6,661,161 | B1 | 12/2003 | Lanzo et al. |
| 6,671,531 | B2 | 12/2003 | Al-Ali et al. |
| 6,678,543 | B2 | 1/2004 | Diab et al. |
| 6,684,090 | B2 | 1/2004 | Ali et al. |
| 6,684,091 | B2 | 1/2004 | Parker |
| 6,697,656 | B1 | 2/2004 | Al-Ali |
| 6,697,657 | B1 | 2/2004 | Shehada et al. |

(56) References Cited

U.S. PATENT DOCUMENTS

| | | |
|---|---|---|
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |

(56) References Cited

U.S. PATENT DOCUMENTS

| | | | |
|---|---|---|---|
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,577,431 B2 | 11/2013 | Lamego et al. |
| 8,581,732 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |

(56) References Cited

U.S. PATENT DOCUMENTS

| | | | |
|---|---|---|---|
| 8,847,740 B2 | 9/2014 | Kiani et al. | |
| 8,849,365 B2 | 9/2014 | Smith et al. | |
| 8,852,094 B2 | 10/2014 | Al-Ali et al. | |
| 8,852,994 B2 | 10/2014 | Wojtczuk et al. | |
| 8,868,147 B2 | 10/2014 | Stippick et al. | |
| 8,868,150 B2 | 10/2014 | Al-Ali et al. | |
| 8,870,792 B2 | 10/2014 | Al-Ali et al. | |
| 8,886,271 B2 | 11/2014 | Kiani et al. | |
| 8,888,539 B2 | 11/2014 | Al-Ali et al. | |
| 8,888,708 B2 | 11/2014 | Diab et al. | |
| 8,892,180 B2 | 11/2014 | Weber et al. | |
| 8,897,847 B2 | 11/2014 | Al-Ali | |
| 8,909,310 B2 | 12/2014 | Lamego et al. | |
| 8,911,377 B2 | 12/2014 | Al-Ali | |
| 8,912,909 B2 | 12/2014 | Al-Ali et al. | |
| 8,920,317 B2 | 12/2014 | Al-Ali et al. | |
| 8,921,699 B2 | 12/2014 | Al-Ali et al. | |
| 8,922,382 B2 | 12/2014 | Al-Ali et al. | |
| 8,929,964 B2 | 1/2015 | Al-Ali et al. | |
| 8,942,777 B2 | 1/2015 | Diab et al. | |
| 8,948,834 B2 | 2/2015 | Diab et al. | |
| 8,948,835 B2 | 2/2015 | Diab | |
| 8,973,580 B1* | 3/2015 | Williams | A61M 16/22 128/204.18 |
| 9,586,015 B1* | 3/2017 | Lindner | A61M 16/0051 |
| 2002/0117173 A1* | 8/2002 | Lynn | A61M 16/0078 128/202.28 |
| 2004/0150525 A1* | 8/2004 | Wilson | G08B 13/2462 340/572.1 |
| 2005/0085799 A1* | 4/2005 | Luria | A61B 5/6803 606/1 |
| 2005/0211761 A1* | 9/2005 | Anttila | A61M 16/22 235/376 |
| 2005/0245836 A1* | 11/2005 | Star | B82Y 10/00 257/253 |
| 2006/0060199 A1* | 3/2006 | Lampotang | A61M 16/0078 128/205.13 |
| 2007/0169780 A1* | 7/2007 | Halpern | A61M 16/0057 128/205.15 |
| 2007/0261698 A1* | 11/2007 | Palatnik | A61B 5/0836 128/207.14 |
| 2008/0053445 A1* | 3/2008 | Kroupa | A61M 16/0078 128/205.23 |
| 2009/0247924 A1 | 10/2009 | Lamego et al. | |
| 2009/0275844 A1 | 11/2009 | Al-Ali | |
| 2009/0299157 A1 | 12/2009 | Telfort et al. | |
| 2010/0004518 A1 | 1/2010 | Vo et al. | |
| 2010/0030040 A1 | 2/2010 | Poeze et al. | |
| 2010/0261979 A1 | 10/2010 | Kiani | |
| 2010/0317936 A1 | 12/2010 | Al-Ali et al. | |
| 2011/0001605 A1 | 1/2011 | Kiani et al. | |
| 2011/0030694 A1* | 2/2011 | Schaner | A61M 16/04 128/207.15 |
| 2011/0082711 A1 | 4/2011 | Poeze et al. | |
| 2011/0105854 A1 | 5/2011 | Kiani et al. | |
| 2011/0208015 A1 | 8/2011 | Welch et al. | |
| 2011/0209915 A1 | 9/2011 | Telfort et al. | |
| 2011/0213212 A1 | 9/2011 | Al-Ali | |
| 2011/0230733 A1 | 9/2011 | Al-Ali | |
| 2011/0237911 A1 | 9/2011 | Lamego et al. | |
| 2012/0059267 A1 | 3/2012 | Lamego et al. | |
| 2012/0116175 A1 | 5/2012 | Al-Ali et al. | |
| 2012/0145151 A1* | 6/2012 | Bergman | A61M 16/0078 128/204.21 |
| 2012/0179006 A1 | 7/2012 | Jansen et al. | |
| 2012/0209082 A1 | 8/2012 | Al-Ali | |
| 2012/0209084 A1 | 8/2012 | Olsen et al. | |
| 2012/0227739 A1 | 9/2012 | Kiani | |
| 2012/0265039 A1 | 10/2012 | Kiani | |
| 2012/0272964 A1* | 11/2012 | Loser | A61B 5/083 128/204.23 |
| 2012/0283524 A1 | 11/2012 | Kiani et al. | |
| 2012/0286955 A1 | 11/2012 | Welch et al. | |
| 2012/0296178 A1 | 11/2012 | Lamego et al. | |
| 2012/0302910 A1* | 11/2012 | Freeman | A61M 16/021 600/538 |
| 2012/0319816 A1 | 12/2012 | Al-Ali | |
| 2012/0330112 A1 | 12/2012 | Lamego et al. | |
| 2013/0023775 A1 | 1/2013 | Lamego et al. | |
| 2013/0045685 A1 | 2/2013 | Kiani | |
| 2013/0046204 A1 | 2/2013 | Lamego et al. | |
| 2013/0041591 A1 | 3/2013 | Lamego | |
| 2013/0060108 A1 | 3/2013 | Schurman et al. | |
| 2013/0060147 A1 | 3/2013 | Welch et al. | |
| 2013/0079610 A1 | 3/2013 | Al-Ali | |
| 2013/0096405 A1 | 4/2013 | Garfio | |
| 2013/0096936 A1 | 4/2013 | Sampath et al. | |
| 2013/0109935 A1 | 5/2013 | Al-Ali et al. | |
| 2013/0162433 A1 | 6/2013 | Muhsin et al. | |
| 2013/0178749 A1 | 7/2013 | Lamego | |
| 2013/0190581 A1 | 7/2013 | Al-Ali et al. | |
| 2013/0197328 A1 | 8/2013 | Diab et al. | |
| 2013/0211214 A1 | 8/2013 | Olsen | |
| 2013/0243021 A1 | 9/2013 | Siskavich | |
| 2013/0253334 A1 | 9/2013 | Al-Ali et al. | |
| 2013/0274571 A1 | 10/2013 | Diab et al. | |
| 2013/0296672 A1 | 11/2013 | O'Neil et al. | |
| 2013/0317370 A1 | 11/2013 | Dalvi et al. | |
| 2013/0324808 A1 | 12/2013 | Al-Ali et al. | |
| 2013/0331670 A1 | 12/2013 | Kiani | |
| 2013/0338461 A1 | 12/2013 | Lamego et al. | |
| 2014/0012100 A1 | 1/2014 | Al-Ali et al. | |
| 2014/0025306 A1 | 1/2014 | Weber et al. | |
| 2014/0034353 A1 | 2/2014 | Al-Ali et al. | |
| 2014/0051952 A1 | 2/2014 | Reichgott et al. | |
| 2014/0051953 A1 | 2/2014 | Lamego et al. | |
| 2014/0051954 A1 | 2/2014 | Al-Ali et al. | |
| 2014/0058230 A1 | 2/2014 | Abdul-Hafiz et al. | |
| 2014/0066783 A1 | 3/2014 | Kiani et al. | |
| 2014/0077956 A1 | 3/2014 | Sampath et al. | |
| 2014/0081100 A1 | 3/2014 | Muhsin et al. | |
| 2014/0081175 A1 | 3/2014 | Telfort | |
| 2014/0085082 A1* | 3/2014 | Lyon | A61B 5/746 340/539.12 |
| 2014/0094667 A1 | 4/2014 | Schurman et al. | |
| 2014/0100434 A1 | 4/2014 | Diab et al. | |
| 2014/0114199 A1 | 4/2014 | Lamego et al. | |
| 2014/0120564 A1 | 5/2014 | Workman et al. | |
| 2014/0121482 A1 | 5/2014 | Merritt et al. | |
| 2014/0121483 A1 | 5/2014 | Kiani | |
| 2014/0125495 A1 | 5/2014 | Al-Ali | |
| 2014/0127137 A1 | 5/2014 | Bellott et al. | |
| 2014/0128696 A1 | 5/2014 | Al-Ali | |
| 2014/0128699 A1 | 5/2014 | Al-Ali et al. | |
| 2014/0129702 A1 | 5/2014 | Lamego et al. | |
| 2014/0135588 A1 | 5/2014 | Al-Ali et al. | |
| 2014/0142401 A1 | 5/2014 | Al-Ali et al. | |
| 2014/0142402 A1 | 5/2014 | Al-Ali et al. | |
| 2014/0163344 A1 | 6/2014 | Al-Ali | |
| 2014/0163402 A1 | 6/2014 | Lamego et al. | |
| 2014/0166076 A1 | 6/2014 | Kiani et al. | |
| 2014/0171763 A1 | 6/2014 | Diab | |
| 2014/0180038 A1 | 6/2014 | Kiani | |
| 2014/0180154 A1 | 6/2014 | Sierra et al. | |
| 2014/0194709 A1 | 7/2014 | Al-Ali et al. | |
| 2014/0194711 A1 | 7/2014 | Al-Ali | |
| 2014/0194766 A1 | 7/2014 | Al-Ali et al. | |
| 2014/0200420 A1 | 7/2014 | Al-Ali | |
| 2014/0200422 A1 | 7/2014 | Weber et al. | |
| 2014/0206963 A1 | 7/2014 | Al-Ali | |
| 2014/0213864 A1 | 7/2014 | Abdul-Hafiz et al. | |
| 2014/0243627 A1 | 8/2014 | Diab et al. | |
| 2014/0266790 A1 | 9/2014 | Al-Ali et al. | |
| 2014/0275808 A1 | 9/2014 | Poeze et al. | |
| 2014/0275820 A1* | 9/2014 | Varga | A61M 16/0078 600/301 |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0275881 A1 | 9/2014 | Lamego et al. | |
| 2014/0288400 A1 | 9/2014 | Diab et al. | |
| 2014/0296664 A1 | 10/2014 | Bruinsma et al. | |
| 2014/0303520 A1 | 10/2014 | Telfort et al. | |

(56) References Cited

U.S. PATENT DOCUMENTS

| | | |
|---|---|---|
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0018650 A1 | 1/2015 | Al-Ali et al. |

* cited by examiner

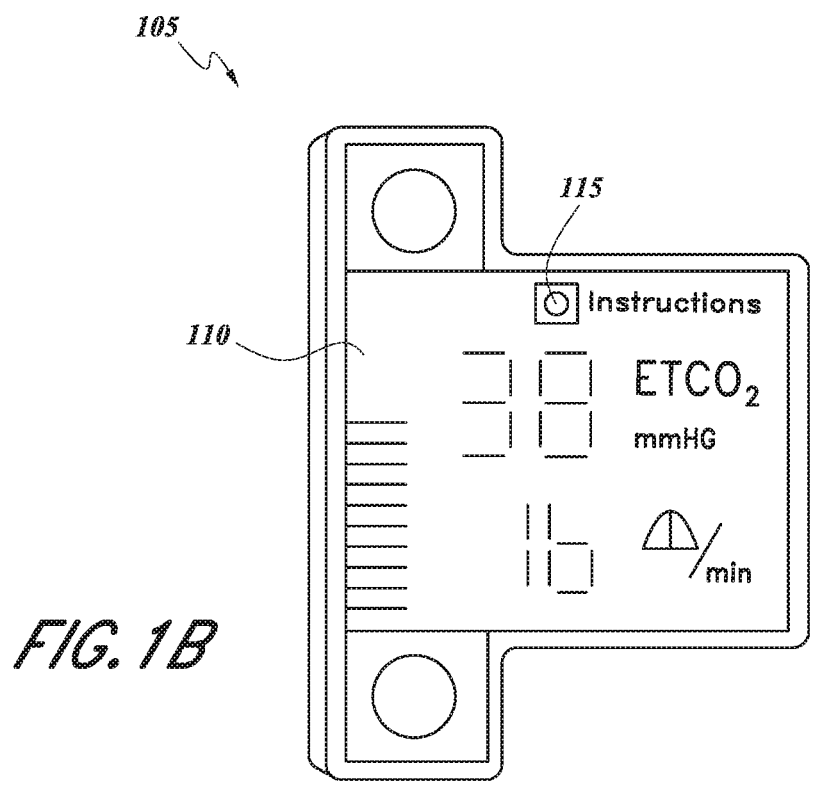
FIG. 1B
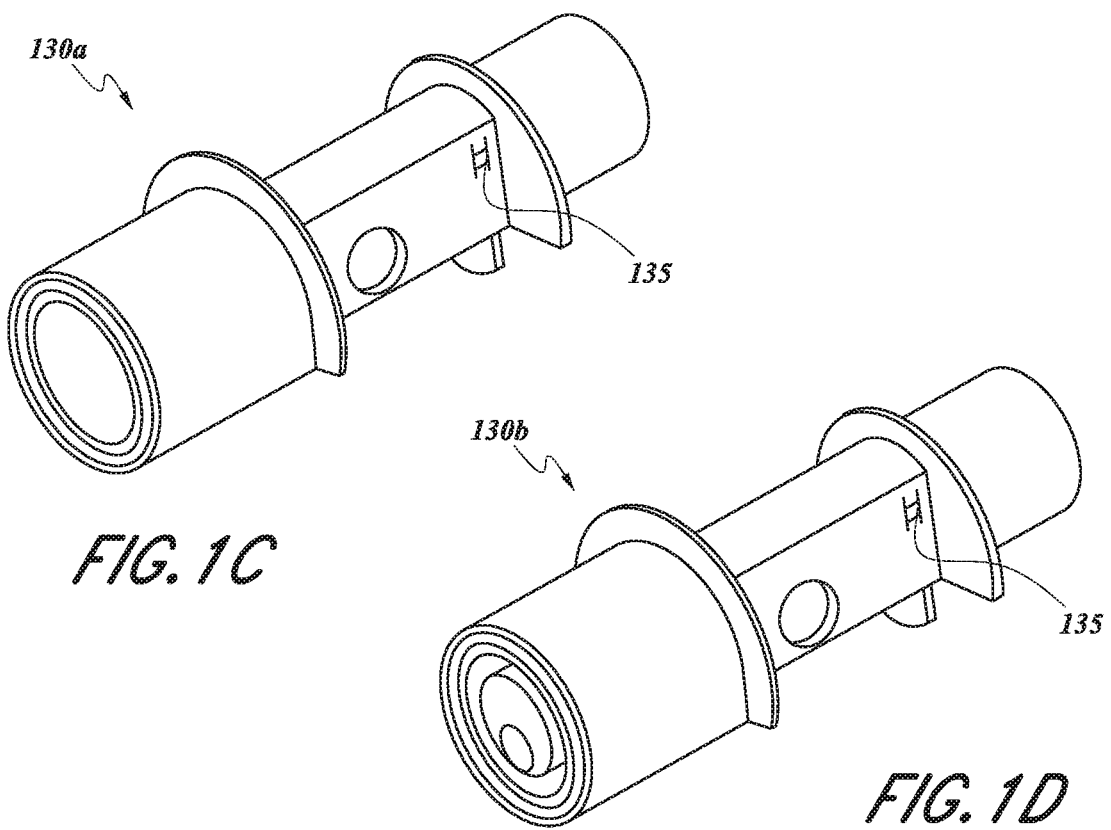
FIG. 1C
FIG. 1D

ASSISTIVE CAPNOGRAPHY DEVICE

INCORPORATION BY REFERENCE TO ANY PRIORITY APPLICATIONS

The present application claims priority benefit under 35 U.S.C. § 119(e) to U.S. Provisional Application No. 61/943,263, titled "DIGITAL INSTRUCTIONS IN CAPNOGRAPHY DEVICE," filed Feb. 21, 2014.

The present application also claims priority to any and all applications for which a foreign or domestic priority claim is identified in the Application Data Sheet as filed with the present application, including without limitation the above-mentioned provisional application, are hereby incorporated by reference in their entirety under 37 C.F.R. § 1.57 and for all purposes.

FIELD OF THE DISCLOSURE

The invention relates generally to systems, devices, and methods for monitoring a patient's respiratory system and health, including capnographers and other devices that monitor patient respiratory gases. In particular, this disclosure relates to respiratory gas measuring devices capable of recognizing attached airway adapters and resuscitation bags and providing assistance for manual ventilation.

BACKGROUND

In respiratory care, it is often desirable to analyze and monitor the gas composition of a patient's exhaled and/or inhaled breathing gases. Various requirements for gas analyses exist in health care. For instance, measurement of respiratory $CO_2$, $O_2$, $N_2O$ and anesthetic agents, such as halothane, isoflurane, enflurane, sevoflurane or desflurane, is useful in the care of critically ill patients undergoing anesthesia or mechanical ventilation, while for emergency care such as manual ventilation it is typically sufficient to monitor breathing of a patient with a simple $CO_2$ analysis.

Respiratory gases can be analyzed in accordance with many different measuring principles. The most common method of respiratory gas analysis, however, is through the medium of non-dispersive spectroscopy. This measuring principle is based on the fact that many gases absorb infrared energy at a wavelength specific to the substance concerned. Main flow gas analyzers based on non-dispersive spectroscopy measure light absorption at specific wavelengths directly in the patient's respiratory circuit. Capnography is the monitoring of the concentration or partial pressure of $CO_2$ in respiratory gases, and provides real-time information regarding $CO_2$ exhalation and respiratory rates as well as a rapid and reliable assessment of a patient's ventilatory, circulatory and metabolic function. Although the terms capnography and capnometry are sometimes considered synonymous, capnometry suggests measurement without a continuous written record or waveform. Typically in capnography and capnometry, a main flow measuring head is placed as close as possible to the patient's mouth or trachea to sample exhaled and/or inhaled breathing gases and calculate gas concentrations directly in the respiratory circuit of the patient.

Measurement of end tidal $CO_2$ can also provide useful information such as regarding $CO_2$ production, pulmonary (lung) perfusion, alveolar ventilation, respiratory patterns, and elimination of $CO_2$ from an anesthesia breathing circuit or ventilator. The gas sample measured at the end of a person's exhalation is called the "end-tidal" gas sample. The amount of carbon dioxide in a person's breath can indicate the overall efficiency of the cardio-pulmonary system and quality of breathing. For example, the concentration of carbon dioxide can indicate shallow breathing and poor oxygen intake. Thus, capnographers are used in hospitals and other medical institutions for monitoring the condition of a patient's respiratory system, pulmonary perfusion, and metabolism, and are most often used for patients in intensive care and under anesthesia.

In many clinical and emergency settings, respiratory assistance is accomplished through use of bag-valve mask (BVM) ventilation systems. Main flow measuring heads can be useful for implementation in BVM ventilation systems and other manual ventilation systems to measure end tidal respiratory gases during respiratory assistance. BVM ventilation is a life-saving skill of an emergency physician or pre-hospital care provider that can easily be overlooked because of its apparent simplicity. However, BVM ventilation is a difficult skill to master, and poor BVM ventilation technique can lead to the need for more invasive means of airway management and their inherent complications. Implementing BVM ventilation with a low rate of bag compression can lead to hypoventilation and inadequate oxygen supply to the patient. Hyperventilation due to over-zealous BVM ventilation can be harmful by increasing intra-thoracic pressure, which decreases venous blood to the heart and subsequently decreases cerebral and coronary perfusion pressures. The appropriate rate of bag compression for proper patient oxygenation differs based on factors such as the age of the patient and the size of the bag. Therefore, there is a need for measuring heads that are capable of providing instructions and feedback to manual ventilation providers.

SUMMARY

Advantageously, in certain embodiments, a physiological monitoring system can be designed to include a respiratory gas measurement head with a processing board or card as well as an airway adapter and resuscitation bag each including an information element that can identify the airway adapter and resuscitation bag to the measurement head. For example, an airway adapter information element can identify the airway adapter to the measurement head as an adult or infant adapter, and a resuscitation bag information element can identify a volume of the resuscitation bag to the measurement head. The system may be connectable to a mobile computing device, such as a smartphone, such that display of the instructions for manual ventilation based on monitored physiological data may occur on the computing device. The board or card may communicate the instructions and data for display with the mobile computing device wirelessly or through a physical and electrical connection with the cable assembly. Alternatively, the measurement head can include a display to provide instructions to the care giver.

Physiological monitoring systems such as are described herein advantageously enable adaptive display of manual ventilation instructions to a medical care provider. This improves patient care and provides a higher likelihood of a positive outcome for the patient. For instance, upon or after assembly of an airway adapter and resuscitation bag to a capnographic measurement head, the measurement head can identify a type of the airway adapter and a volume of the resuscitation bag. In one example, a processor of the measurement head can perform the identification by communicating with an information element located on one or both of the airway adapter and the resuscitation bag. The identification of the adapter and ventilation bag can provide many useful parameters. For example, the parameters can include, for example, the type of patient, such as an adult patient or an infant patient, the volume of the bag, the length of the airway adapter and any other useful parameters helpful in determining proper operation of the manual ventilation system. As a result of being able to identify the airway adapter and resuscitation bag, the measurement head provides appropriate instructions for the parameters of the manual ventilation system.

The present disclosure allows a medical care provider to receive real time (or near real time) feedback regarding their manual ventilation efforts through analysis of the patient's physiological data such as end tidal gas values taking into account the characteristics of the adapter airway and resuscitation bag. To illustrate, a resuscitation bag that is identified as having a high volume should be compressed more slowly and/or less frequently than a resuscitation bag identified as having a small volume in order for appropriate oxygen delivery to the patient. The present disclosure allows the ventilation system to provide feedback to pace the caregiver's efforts. Further, for an individual who is untrained in manual ventilation but is called to perform such techniques in an emergency setting, the present system provides critical manual ventilation instructions based on real time monitored conditions of the patient.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Throughout the drawings, reference numbers can be re-used to indicate correspondence between referenced elements. The drawings are provided to illustrate embodiments of the inventions described herein and not to limit the scope thereof.

FIG. 1B illustrates an embodiment of a measuring head.

FIG. 1C illustrates an embodiment of an airway adapter.

FIG. 1D illustrates another embodiment of an airway adapter.

DETAILED DESCRIPTION

I. Example Physiological Monitoring Systems

Figure 1A:
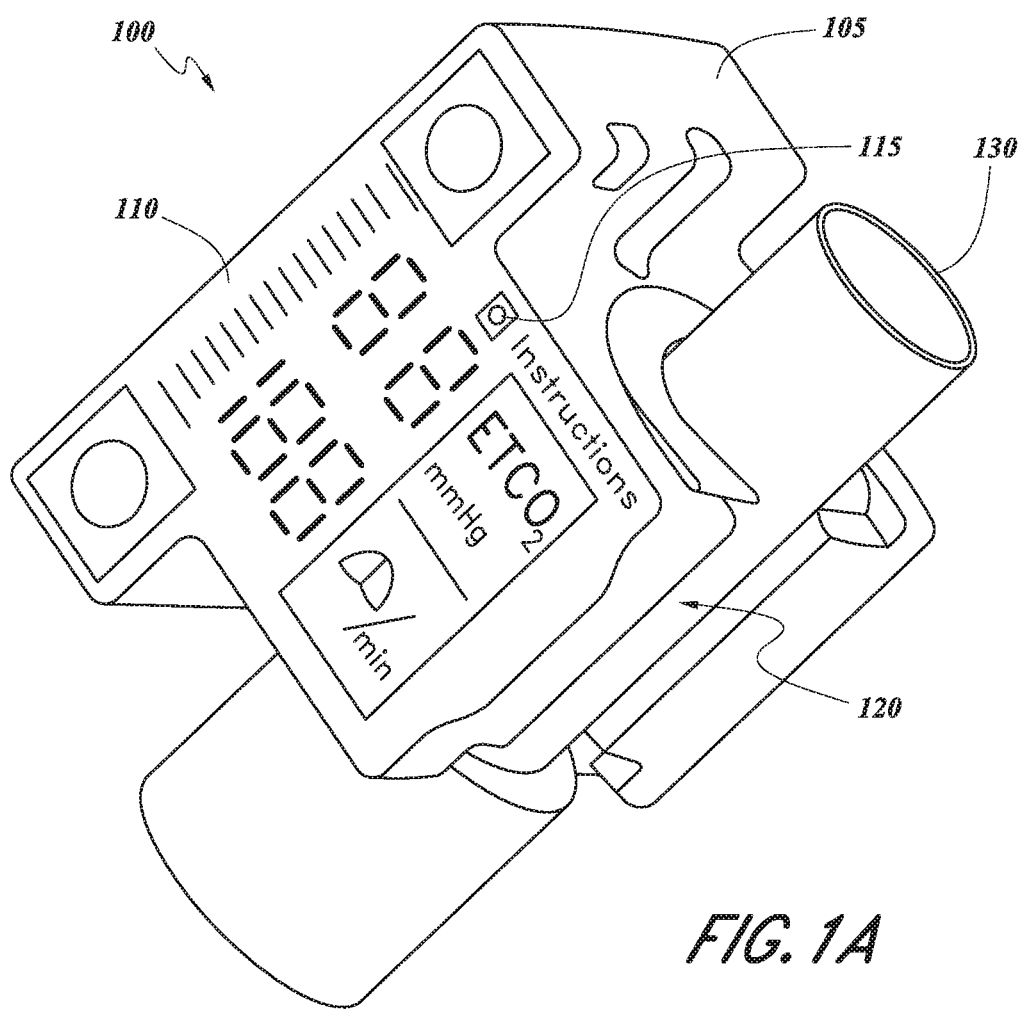
FIG. 1A illustrates an embodiment of a physiological monitoring system.

FIGS. 1A-1D illustrate embodiments of a physiological monitoring system 100. The physiological monitoring system 100 shown in FIG. 1A includes a capnographic measurement head 105 and an airway adapter 130. The measurement head 105 can include a display 110 having an indication 115 regarding when instructions are available and a connection port 120 for insertion of the airway adapter 130. FIG. 1B illustrates an example of the measurement head 105 illustrated without an airway adapter in place. FIG. 1C illustrates an example of an airway adapter 130a that can be used in adult or pediatric ventilation assistance, the airway adapter 130a includes an information element 135. FIG. 1D illustrates an example of an airway adapter 130b that can be used in infant or neonate ventilation assistance, the airway adapter 130b has an information element 135.

The physiological monitoring system 100 can be used to monitor physiological parameters such as end tidal respiratory gases including oxygen ($O_2$), carbon dioxide ($CO_2$), and nitrous oxide ($N_2O$), among others, as well as patient respiratory rate. A system capable of measuring these parameters is commercially available from Masimo Corporation of Irvine, Calif., marketed under the name EMMA™. The physiological monitoring system 100 can also measure anesthetic agents and perform agent identification in some examples. The physiological monitoring system 100 can be used for proof of intubation (that is, to show that an endotracheal tube has been correctly placed in the trachea, and not the esophagus, of a critically ill patient), short-term $CO_2$ monitoring for ventilation during emergency patient transport, $CO_2$ monitoring during cardiopulmonary resuscitation (CPR), among other uses.

The measurement head 105 can be configured to analyze respiration rate and concentration of gases in a patient's exhaled respiratory gases, among other things. Some embodiments of the measurement head 105 can be compact, portable for flexible use at multiple points of care including pre-hospital, emergency medicine, operating rooms, intensive care units, and long-term acute care. The measurement head 105 can be provided with display 110 for illustrating monitored physiological parameters to a clinician. Although end tidal $CO_2$ and respiratory rate in breaths per minute are illustrated in the example display 110, other embodiments can analyze and display these and/or the additional parameters discussed above. In addition, in some embodiments the measurement head 105 can be configured to communicate with an external display. In some embodiments, the display 110 may be omitted. Display 110 also includes an indicator 115 to highlight to a clinician when usage instructions are available for a connected airway adapter and/or resuscitation bag, as will be discussed in more detail below. The measurement head 105 can also be provided with visual and/or audible alarms, a capnograph waveform display, and various user interface features such as a power button. Some embodiments of the measurement head 105 may be battery operated and contain a power source housing.

As in the illustrated embodiment, the measurement head 105 can be a mainstream capnometer or capnographer placed directly into a patient's airway or coupled to an airway adapter 130 placed in the patient's airway. The measurement head 105 can house an infrared light source and photodetector in some embodiments, such as a non-dispersive infrared gas analyzer. The measurement head 105 can be, in other embodiments, a sidestream capnometer or capnographer sampling a patient's respiratory gases through a tube or lumen from the patient's airway to the measurement head 105.

The airway adapter 130 can be provided for insertion into or placement adjacent the patient's mouth. The airway adapter 130 is configured to transfer or guide gases exhaled from the patient to the measuring head 105. In some embodiments, the airway adapter 130 can be about 1 inch, about 2 inches, about 4 inches, or about six inches long. In other embodiments, the airway adapter 130 can be no longer than about 5 inches. As illustrated in FIGS. 1C and 1D, the airway adapter can have different configurations for patients of different ages. For example an airway adapter such as airway adapter 130a can be used in adult or pediatric ventilation assistance, while an airway adapter such as airway adapter 130b can be used in infant or neonate ventilation assistance. In some embodiments, the airway adapter 130 can be replaceable and/or disposable while the measurement head 105 is reusable. The airway adapter 130 may have a hydrophilic inner surface to create a film of water condensed from a patient's exhaled breath such that the film does not scatter an infrared beam used to measure gas concentrations. The inner surface can also be etched in some embodiments to further control the formation of condensation within the airway adapter 130.

The airway adapter 130 can be placed into connection port 120 in the measuring head 105 to provide fluid communication between a patient's respiratory circuit and a measuring chamber of the measurement head 105. Exhaled respiratory gases can pass into the airway adapter 130 through a breathing mask or a sampling line, and the exhaled gases can pass through an output opening in a side of the airway adapter into a measuring chamber of the measurement head 105. In one example, the measuring chamber of the measurement head 105 can be compressed to a size of 50 µl to provide accurate measurements under extreme conditions, such as for young patients with very high breathing rates, delivering approximately a 50 mL/min sampling flow that can accommodate respiratory monitoring for patients of a wide range of ages, from adults to neonates.

The measurement head 105 can be configured to measure a physiological parameter of the patient by analyzing the respiratory gases in the measuring chamber. In one implementation of gas analysis, the light from an infrared emitter can pass through the gas mixture in the measuring chamber and the light can be filtered by a narrow-band optical band-pass filter. The gases can absorb the infrared light at known, gas-specific wavelengths during passage of the light through the gas mixture. The partially absorbed light can be detected by an infrared detector and the intensity of the detected light can be determined, for example by a processor of the measurement head 105 or by the processor of another computing device. By measuring the intensity of the light that was not absorbed into the gas mixture, a quantification of the concentration of a gas or gases in the gas mixture can be obtained. In this manner, an embodiment of the measurement head 105 can analyze an unknown gas mixture and identify which gases and/or agents are present in the mixture.

Accordingly, the measurement head 105 can include an emitter, an optical filter, and at least one sensor (not illustrated) for conducting analysis of gas concentrations in respiratory gas samples received from the airway adapter 130. The emitter, filter, and sensor can be positioned in the measuring chamber within the measurement head 105, for example near the output opening in the airway adapter. An emitter can be configured to emit light at one or more wavelengths into a measuring chamber containing a gas sample, and a sensor can be configured to detect the emitted light. An optical filter (not illustrated) can be included in the measurement head 105. For example, the filter can be a narrow band optical filter, and can be manufactured using a film deposition process that can balance out film layer thickness variations created by changes in temperature in order to reduce center wavelength drift with temperature.

A sensor, such as an infrared detector, can be included in the measurement head 105 to receive the light emitted by the emitter. In one embodiment, the sensor or sensors can be a spectrometer used to detect slight changes in infrared radiation to precisely determine gas concentrations in a mixture by measuring absorption caused by molecules in the gas sample. In some embodiments, the spectrometer can detect changes in multiple wavelengths of light, for example at nine different wavelengths in the long-wavelength infrared (LWIR) spectrum. The LWIR wavelength band contains strong absorption peaks for CO2, N2O, and various anesthetic agents, with negligible interference from alcohol, acetone, and other gases and vapors that could potentially degrade measurement accuracy. In another embodiment, the sensor(s) can be carbon dioxide sensors, for example nanotechnology carbon dioxide sensors, nanoelectric sensors, pyroelectric detectors, thermopile detectors, or infrared sensors. In multigas monitoring embodiments of the measurement head 105, the sensor(s) can be configured to trace gas sample compositions across multiple pre-selected narrow band optical filters. In some embodiments multiple sensors may be mounted in a thermally stable array, for example a block of aluminum.

The measurement head 105 can also include a processor (not illustrated) generally including circuitry that can process the physiological parameter signal(s) generated by the sensor(s) prior to display or storage of the parameters. The processor can include instructions to process analog pressure, temperature, and flow signals combined with data from the sensor(s). The processor can analyze the data received from the sensor(s) and determine a physiological parameter or parameters of the patient. For example, the processor can include any of a variety of front-end signal conditioners, such as filters, amplifiers, buffers, memories and/or analog-to-digital (A/D) converters known to those of skill in the art. The processor can extract one or more optical filter signals from the sensor data and can filter the signal(s) to remove noise in some embodiments, such as high and low frequency noise. The processor can analyze the sensor data and/or filtered data to determine gas and agent identification and measurement. In one example, the processor can be a 32-bit RISC microprocessor. In another example, the processor can be a 41-MIPS RISC DSP and can provide power to a spectrometer of the measurement head 105. The processor can be designed to be compact and power-efficient in some embodiments. The processor can be a digital signal processor (DSP) or analog processor or combination of both.

The processor can also include instructions to communicate with the information element 135 of an airway adapter 130, the information element of a resuscitation bag, and/or the information element of another respiratory assistance component. Such information elements can be placed at any location on the airway adapter or resuscitation bag that can be in electrical contact with the measurement head 105, and the measurement head 105 can have corresponding reading element(s) for contacting the information element(s).

Though discussed primarily in the context of airway adapters and resuscitation bags, such information elements can be provided on any ventilation assistance component such as gas sampling lines and breathing masks, to name a few other examples.

In some embodiments, the processor of the measuring head 105 can read data stored on an information element upon or after physical and electrical connection to the corresponding reading element. The processor can use the data to identify an attached ventilation assistance component. The information element 133 can be an active circuit such as a transistor network, memory chip, EEPROM (electronically erasable programmable read-only memory), EPROM (erasable programmable read-only memory), or other identification device, such as multi-contact single wire memory devices or other devices, such as those commercially available from Dallas Semiconductor or the like. The information element can be, in some embodiments, a resistor, a capacitor, a microchip, a RAM, a ROM, or any other information storage element. In addition, the information element can include a combination of one or more of any of the above.

In other embodiments, the processor and information element may communicate wirelessly. For example, radio communications can be used to identify an attached ventilation assistance component and/or its characteristics. In one embodiment, radio-frequency identification (RFID) can enable communication between an information element and the processor. A passive RFID tag can be included in or on an airway adapter and/or resuscitation bag, the tag containing electronically stored information. The RFID tag can act as a passive transponder to emit radio waves that can be detected by an active reader element associated with the processor of the measurement head. In another embodiment, near field communication (NFC) technology can enable communications between an unpowered NFC chip on an airway adapter or resuscitation bag and an NFC reading component communicating with the measurement head processor. As another example, the measurement head can be equipped with an optical scanning means for scanning a barcode, matrix barcode, or other optical machine-readable representation of data on an airway adapter or resuscitation bag. In some embodiments, various ventilation assistance components can implement the same or different communication means as discussed above.

An information element can store information specific to the corresponding ventilation accessory component. For example, an airway adapter information element 135 can include data to identify an intended age group of the airway adapter, for example by identifying the airway adapter as one of an adult/pediatric airway adapter 130a or an infant/neonate airway adapter 130b. Such information can be used by the processor to provide age-specific ventilation instructions to a clinician. Though two examples of airway adapters are illustrated in FIGS. 1C and 1D, other sizes of airway adapters are possible in other embodiments. As another example, a resuscitation bag information element can include data to identify characteristics of the resuscitation bag such as volume, compressive resistance, or the like. Such information can be used by the processor to provide instructions regarding compression rate and compression depth, as well as other manual ventilation techniques. Such information elements can also be used to store instructions specific to the component to which they are attached.

In addition, such information elements can store information about the use of the airway adapter or resuscitation bag in order to prevent overuse or reuse. During use, airway adapters and resuscitation bags collect condensation from a patient's exhaled respiratory gases. As such, it can be unsanitary to reuse such components from patient to patient. Accordingly, an information element can store data indicating that the component has already been attached to a measurement head, and therefore has presumably been used. In some embodiments, the measurement head may not perform measurements when a used component is detected and/or may output an indication to replace the component with a new component.

The instructions can enable clinicians to assess the effectiveness of cardiopulmonary resuscitation (CPR) and can guide manual ventilation. For example, the measurement head 105 can use the physiological data to determine whether adequate ventilation is occurring, and the measurement head 105 can use communications with a resuscitation bag information element to provide feedback on the depth and effectiveness of compressions of the resuscitation bag. As another example, the measurement head 105 can use communications with an airway adapter information element 135 to provide ventilation instructions appropriate for the patient's age group based on whether the airway adapter is an adult airway adapter 130a or an infant airway adapter 130b.

Some embodiments of display 110 can be sized and configured to display the instructions on the measurement head 105. In other embodiments the processor may communicate the instructions to an external display, such as a medical terminal or a clinician's mobile device. The instructions can be a graphical representation of compression rate and compression depth in one example. As another example, an auditory signal can be provided to guide compression rate and compression depth. Indications of the quality of manual ventilation technique can be provided including an alarm, an icon, or a color that generally represents the quality of a measured physiological parameter. The instructions can include, in some embodiments, instructions for proper assembly of the physiological monitoring system 100 and/or proper placement on a patient. The measurement head 105 can update or alter the instructions during the course of manual ventilation assistance based at least partly on the physiological data of the patient in some embodiments.

Figure 2A:
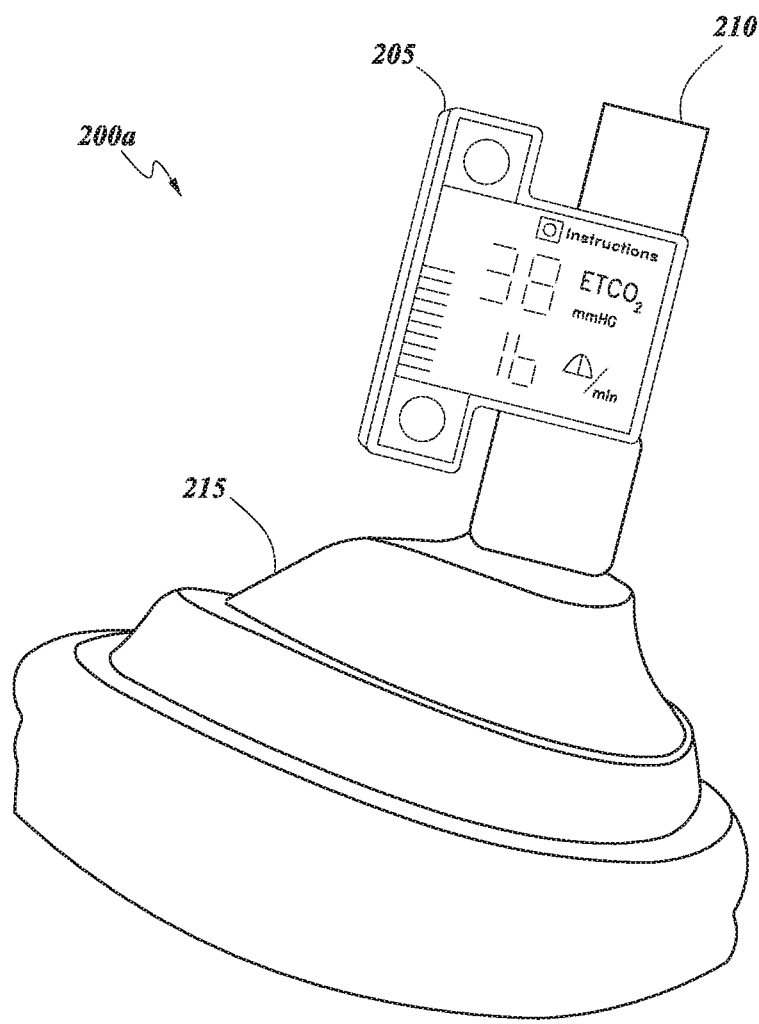
FIGS. 2A-2B illustrate various embodiments of a ventilation assembly.

The system 200a as illustrated in FIG. 2A shows a measuring head 205 coupled to an airway adapter 210, with the airway adapter 210 coupled to a breathing mask 215. The system 200a can be placed over a patient's mouth for safe delivery of rescue breaths during CPR, for example during cardiac arrest or respiratory arrest. The system 200a can also be attached to other manual or mechanical ventilation components.

Figure 2B:
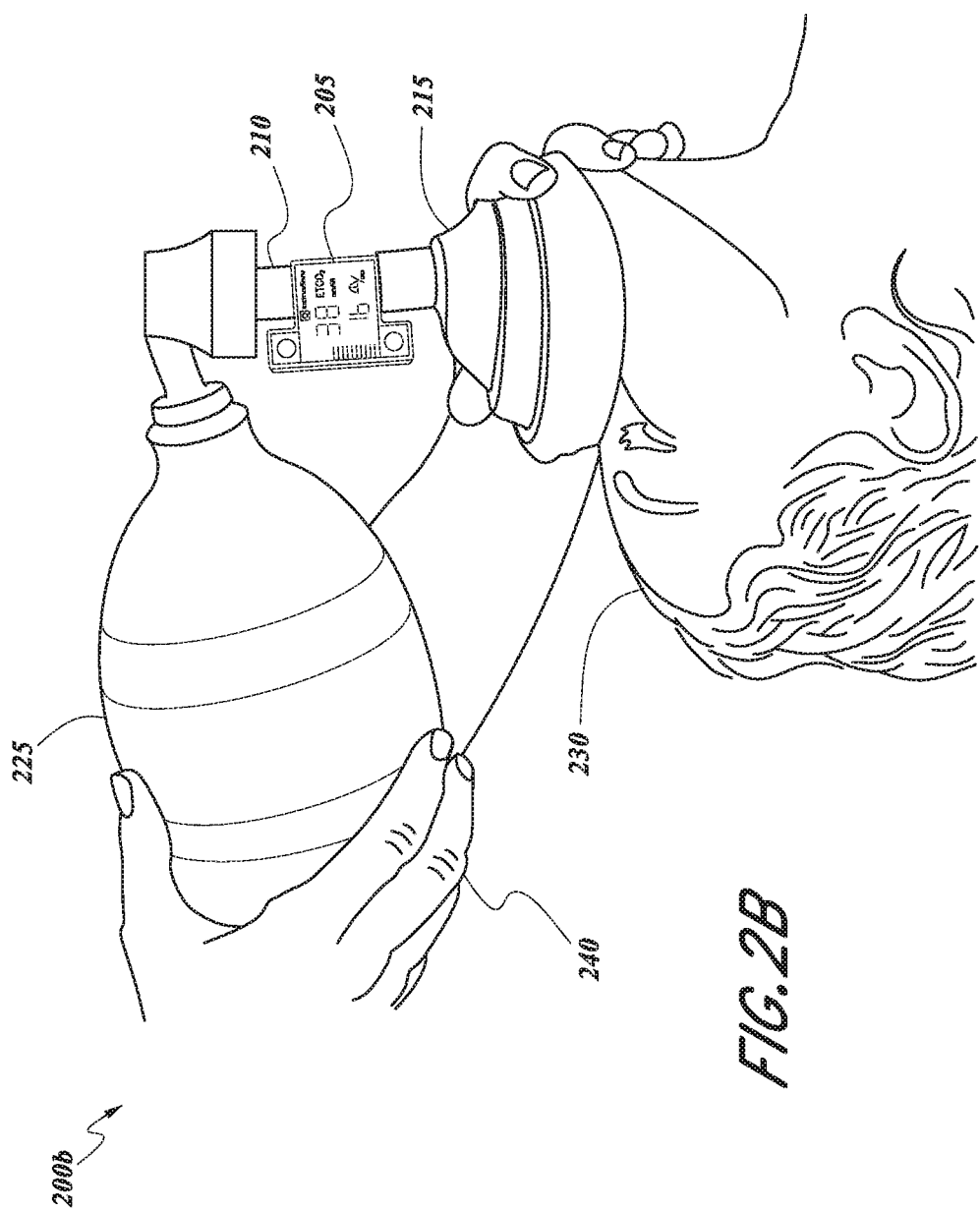

The system 200b as illustrated in FIG. 2B shows a measuring head 205 coupled to an airway adapter 210, with the airway adapter 210 coupled to a breathing mask 215, similar to the system 200a of FIG. 2A. The system 200b also includes a resuscitation bag 225 coupled to the airway adapter 210 for operation by a care provider 240. The breathing mask 215 of system 200b is illustrated placed over a patient's 230 mouth for delivery of manual ventilation therapy. A care provider must ensure that the mask is substantially sealed around the patient's face such that pressure needed to force-inflate the lungs is not released into the environment. Though illustrated with a mask 215 over a patient's mouth, other implementations of the system 200b can be adapter for connection to an endotracheal tube or laryngeal mask airway.

System 200b can be used to provide positive pressure ventilation to patients who are not breathing or are not breathing adequately without assistance. The resuscitation bag 225 acts as a flexible air chamber that, when squeezed, forces air through a one-way valve into the patient's lungs. When released, the resuscitation bag 225 self-inflates through the end not coupled to the airway adapter 210, drawing in either ambient air or an oxygen flow supplied by a regulated cylinder, while also allowing the patient's lungs to deflate to the ambient environment.

The system 200*b* can be available in different sizes to fit infants, children, and adults in some embodiments. The sizes of the face mask 215, airway adapter 210, and bag 225 may vary independent of one another. For example, a pediatric sized bag might be used with different masks for multiple face sizes, or a pediatric mask might be used with an adult sized bag for patients with smaller faces. In order to be effective, a bag valve mask must generally deliver between 500 and 800 ml of air to a normal male adult patient's lungs, however if supplemental oxygen is provided 400 ml may still be adequate. This amount can vary for females, children, and infants. Generally, squeezing the bag once every 5-6 seconds for an adult or once every 3 seconds for an infant or child can provide adequate respiratory rate (determined as 10-12 respirations per minute in an adult and 20 per minute in a child or infant). As such, based on the patient as well as the size of the face mask 215, airway adapter 210, and bag 225, a care provider performing the manual ventilation is required to use different compression rates and depths of compression in order to provide suitable ventilation assistance. The presently described device can provide feedback to a user based on current patient parameters and device parameters in order to assist a user to provide optimal manual ventilation to a patient.

Figure 3:
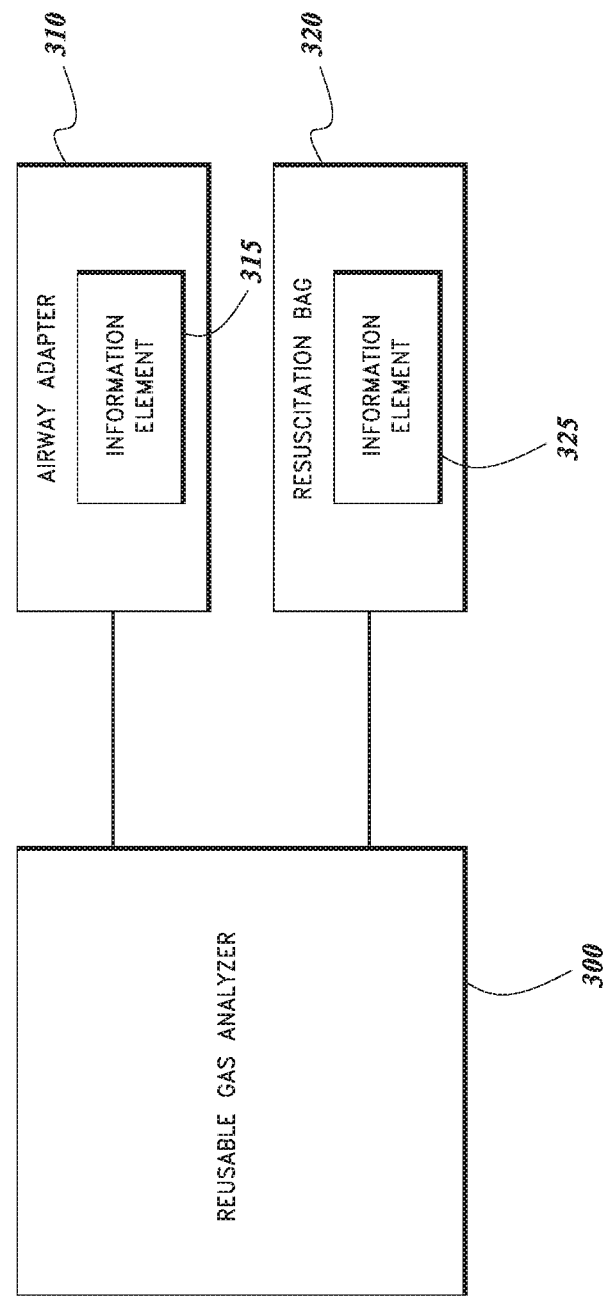
FIG. 3 illustrates a schematic block diagram of one embodiment of a physiological monitoring system.

FIG. 3 illustrates a schematic block diagram of one embodiment of a physiological monitoring system including a reusable gas analyzer 300, an airway adapter 310, and a resuscitation bag 320. The airway adapter 310 includes an information element 315 and the resuscitation bag 320 includes an information element 325. As discussed above, the information element 315 can serve to identify characteristics of the airway adapter 310 to the reusable gas analyzer 300, and the information element 325 can serve to identify characteristics of the resuscitation bag 320 to the reusable gas analyzer 300.

Information element 315 can store data identifying characteristics of the airway adapter 310. For example, the data can include a size of the airway adapter 310 such as adult, child, infant, or neonatal. The data can also include a type of the airway adapter such as an airway adapter designed to connect to a breathing mask or an airway adapter designed to connect to an endotracheal tube. In some embodiments, the data can include information regarding a manufacturer of the airway adapter 310. This data can be used to determine whether to recommend instructions to a care provider and/or which instructions to recommend to a care provider. For example, an airway adapter 310 from a known manufacturer may be associated with a specific set of instructions, while an airway adapter 310 from an unknown manufacturer may not be associated with instructions. As another example, an infant airway adapter may be associated with instructions for a more rapid rate of compression relative to the instructions associated with an adult airway adapter. Information element 315 can store data representing instructions associated with use of the airway adapter 310 in some embodiments. In an embodiment, the information can store a formula or algorithm that the measurement head can use in addition to other data to determine proper compression rates. For example, the information from the airway adapter can be combined with end tidal $CO_2$ to determine an adjusted compression rate depending on the patient's responsiveness.

Information element 325 can store data identifying characteristics of the resuscitation bag 320. For example, the data can include a size or volume of the resuscitation bag 320 corresponding to an adult, child, infant, or neonatal patient's lung volume and respiratory needs. Adult bags, in some embodiments, can deliver volumes of 240-2,000 ml of room air or oxygen with each compression. Child and infant bags can be designed to deliver smaller volumes of room air per compression. In some embodiments, the data can include information regarding a manufacturer of the resuscitation bag 320. This data can be used to determine whether to recommend instructions to a care provider and/or which instructions to recommend to a care provider. For example, a resuscitation bag 320 from a known manufacturer may be associated with a specific set of instructions, while a resuscitation bag 320 from an unknown manufacturer may not be associated with instructions. As another example, an infant resuscitation bag may be associated with instructions for a more rapid rate of compression relative to the instructions associated with an adult resuscitation bag. Compression rate and depth instructions can also be based on a comparison of a volume of the resuscitation bag as communicated by the information element 325 and an age or size of the patient as input by a care provider. Information element 325 can store data representing instructions associated with use of the resuscitation bag 320 in some embodiments.

Information elements 315, 325 can be provided through a circuit that contacts a corresponding portion in the reusable gas analyzer 300, for example a transistor network, memory chip, EEPROM (electronically erasable programmable read-only memory), EPROM (erasable programmable read-only memory), multi-contact single wire memory device, a resistor, a capacitor, a microchip, a RAM, or a ROM, or any other information storage element. Information elements 315, 325 can also be provided through a wireless communication means such as RFID or NFC, or through optical scanning technology. Information elements 315, 325 can be configured using the same or different technologies. For example, in some embodiments information element 315 of the airway adapter 310 may be in physical contact with the reusable gas analyzer 300, while information element 325 of the resuscitation bag 320 may communicate wirelessly with the reusable gas analyzer 300.

The reusable gas analyzer 300 may communicate with the information elements 315, 325 once in some embodiments, for example upon connection of the airway adapter 310 and resuscitation bag 320, or when the information elements 315, 325 are in wireless communication range. In some embodiments the reusable gas analyzer 300 may communicate with the information elements 315, 325 when powered on. In other embodiments reusable gas analyzer 300 may communicate with the information elements 315, 325 at various points during ventilation therapy.

Figure 4A:
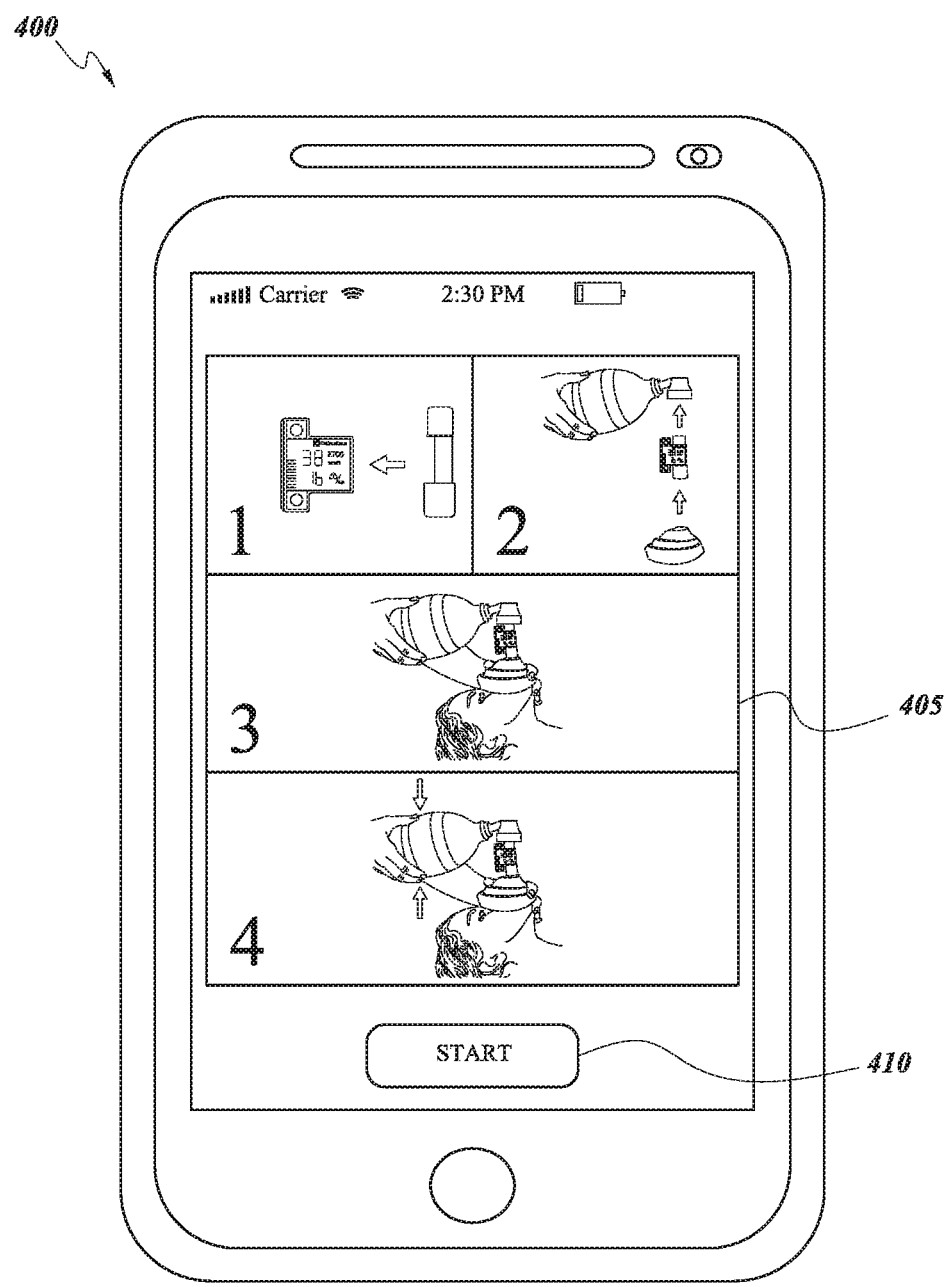
FIG. 4A illustrates an embodiment of a software application for display of ventilation instructions.

FIG. 4A illustrates an embodiment of an application for display and management of manual ventilation instructions 405 and also, in some embodiments, physiological monitoring data. Some embodiments of the software application may be used with a mobile computing device of a clinician, illustrated here as smartphone 400. Although specific reference may be made to smartphones in this disclosure, persons skilled in the art will understand that a mobile computing device compatible with the physiological sensor system may be one of a wide range of mobile devices such as a laptop, tablet computer, netbook, PDA, media player, mobile game console, stationary or portable medical terminal, or other microprocessor based device configured to interface with a physiological sensor. Some embodiments of the mobile computing device may be used with the system for display of instructions and/or data as well as storage of data. Cables used to connect smartphone 400 to a reusable gas analyzer (for example, measurement head 105 of FIG. 1 discussed above) can be flex cables or other cables, including cables having triboelectric properties, and some devices may be configured to connect wirelessly to the reusable gas analyzer.

Smartphone 400 may include a display screen such as an LED or LCD screen, and may include touch sensitive technologies in combination with the display screen. Smartphone 400 may include software configured to display manual ventilation instructions 405 as well as some or all of the output measurement data on the display screen. The instructions can include steps for proper assembly or placement of a ventilation assistance system and/or steps for operation of the ventilation assistance system. The operation steps can be based on data read from information elements on components of the ventilation assistance system, as discussed above. A measurement data display may comprise numerical or graphical representations of end tidal $O_2$, $CO_2$, $N_2O$, and/or patient respiratory rate and some embodiments may simultaneously display numerical and graphical data representations.

The smartphone 400 may include software such as an application configured to enable interaction with the instructions 405 as well as to manage output measurement data from the measurement head processing module. The instruction application functionality can include provision of assembly or operation instructions prior to and during ventilation assistance, allowing clinician input of patient and/or equipment characteristics, and provision of feedback during ventilation assistance based on physiological parameters. The data management functionality of the application can include trend analysis, current measurement information, alarms associated with above/below threshold readings, reminders to take measurement data at certain times or cycles, display customization, iconic data such as hearts beating, color coordination, bar graphs, gas bars, charts, graphs, or the like, all usable by a caregiver or smartphone user to enable helpful and directed medical monitoring of specified physiological parameters.

In some embodiments, software capable of analyzing the output measurement data received from the processing module and making the data available in an appropriate manner health management is installed on the smartphone 400. The smartphone 400 may also be able to alert the user to an abnormal data reading and to update the manual ventilation instructions 405 accordingly. For example, an abnormally low or high carbon dioxide reading may cause the smartphone 400 to buzz, vibrate or otherwise notify the user of an abnormal reading. The smartphone 400 can also issue a graphical warning. In some embodiments, the instructions can be updated based on the abnormal reading to provide an updated compression rate and/or compression depth for a resuscitation bag.

The smartphone 400 can include graphical instructions 405 for review by the clinician prior to manual ventilation therapy as well as a selectable option 410 to begin therapy. In some embodiments, the smartphone 400 can determine that therapy has begun based on input physiological parameter data and the option 410 can be omitted. The instructions 405 can be replaced or supplemented, upon commencement of ventilation therapy, with a compression rate and/or compression depth indicator providing visual or auditory feedback to a provider regarding depth and timing of resuscitation bag compressions.

Figure 4B:
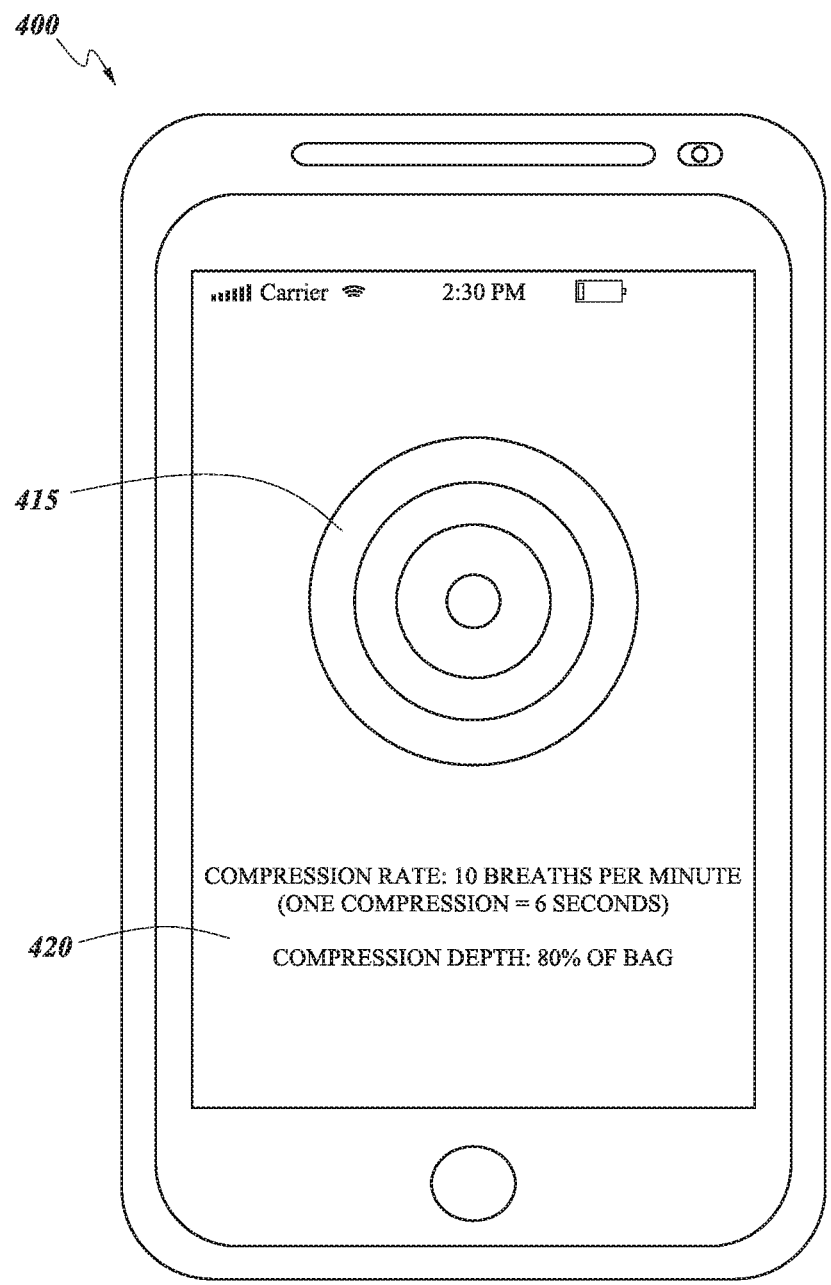
FIG. 4B illustrates another embodiment of a software application for display of ventilation instructions.

For example, as illustrated in FIG. 4B, a visual indicator 415 can be accompanied by text 420 in one embodiment indicating compression rate and compression depth determined to be suitable for the patient based at least partly on the information elements. Some embodiments of the software application may also allow for input by a physician or other care provider and can use the input to determine the compression rate and compression depth. The visual indicator 415 can be, in one example, a plurality of concentric circles. In some embodiments, the circles can be sequentially illuminated from the outer circle toward the inner circle to simulate squeezing of the resuscitation bag in order to provide a physician with visual feedback regarding depth and timing of compressions. The text 420 can indicate to the physician compression rate in breaths per minute, a length of time for each compression, and a percentage of compression of the bag, among other things.

In certain embodiments, a software application for presenting resuscitation instructions may be downloadable from a computer network at a cost, by subscription, pay-per-use, or the like. Other embodiments may advantageously be incorporated into caregiver-specific applications which include reminders for timed measurements or protocols. For example, a caregiver for a surgical patient may desire measurement data at regular intervals to assess the presence and effects of anesthetic agents. A caregiver-specific application may be advantageously programmed to accomplish such a protocol. Other caregiver-specific applications may provide animated or textual instructions, links to online information regarding certain monitoring situations, ailments, or other useful patient research.

FIGS. 5A-5D illustrate various embodiments of display interfaces on a respiratory gas analyzing measuring head 500. The measuring head 500 comprises a display 505, which may include a plurality of display portions in which a plurality of physiological parameters may be displayed, such as end tidal carbon dioxide ($ETCO_2$) and respiratory rate. The display 505 can also include a portion for manual ventilation compression instructions 510. The configuration of these various display portions is meant for illustrative purposes, and one skilled in the art would appreciate that the parameter and instruction displays could be rearranged relative to one another, displayed alone, or the user interface could be modified to include other parameter display portions. Further, although some of the parameter display portions employ numerical representations of the physiological data, some embodiments may employ graphical representations, for example a contracting/expanding lung icon may indicate respiratory rate.

Figure 5A:
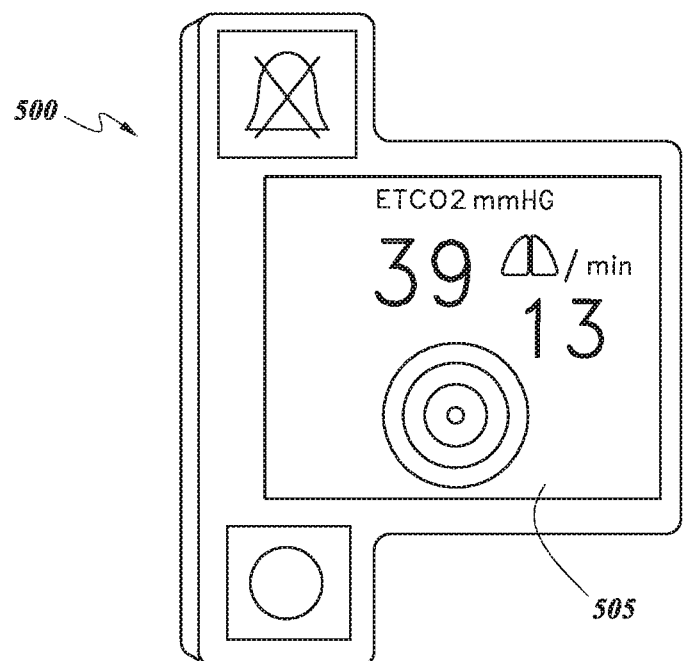
FIGS. 5A-5D illustrate various embodiments of display interfaces on a measuring head.
Figure 5B:
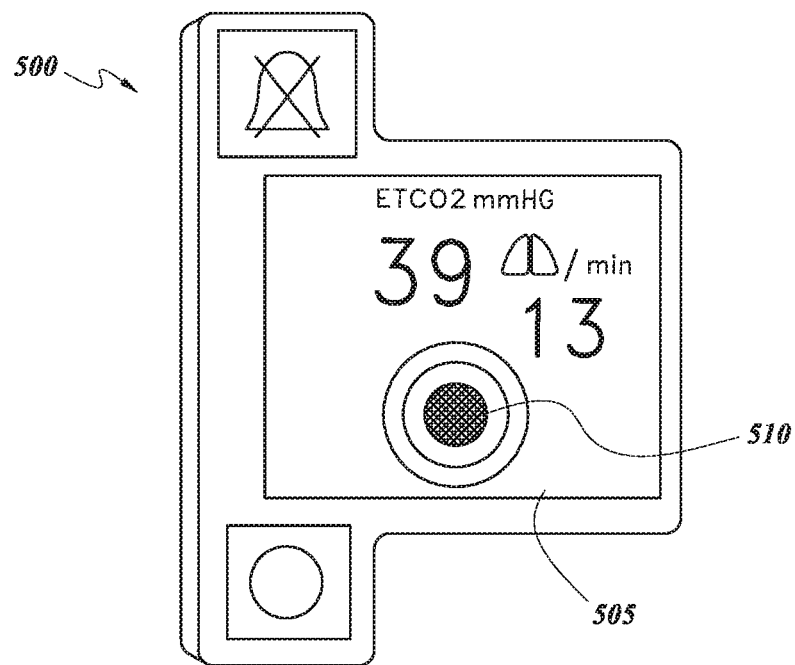

As illustrated in FIG. 5A and FIG. 5B, manual ventilation compression instructions 510 can be graphically represented using a plurality of concentric circles in one embodiment. The circles can be sequentially illuminated or filled from the inner circle towards the outer circle in some embodiments to indicate compression rate and compression depth. To illustrate, in one embodiment the timing between the innermost circle first being illuminated, the expansion of the illumination toward the outer circle, and the contraction of the illumination toward the inner circle until no circle is illuminated can correspond to the length of time for one compression and decompression of a resuscitation bag. As the illumination begins expanding outward the clinician can slowly apply pressure on the resuscitation bag. When the illumination reaches its outermost point and begins contracting inward the clinician can slowly release pressure on the resuscitation bag. As another illustration, the amount of illumination of compression instructions circles can correspond to an amount of compression applied to the resuscitation bag in some embodiments. When no circles are illuminated, no compression should be applied to the bag. When the outermost circle is illuminated the bag should be fully compressed. When circles between the inner and outer circle are illuminated, the bag should be partially compressed corresponding to the positioning of the largest illuminated circle relative to the outer circle. According to one embodiment of the instructions, a bag may not need full compression for suitable patient ventilation so the outermost circle would not be illuminated. In other embodiments, the circles can be sequentially illuminated from the outer circle toward the inner circle to simulate squeezing of the resuscitation bag. Similarly, the circles can be sequentially un-illuminated from the inner circle to the outer circle as the bag is decompressed.

The compression rate and/or compression level can be set at the initialization of instructions based on data read from the information element of an attached airway adapter and/or resuscitation bag. The compression rate and/or compression level can be varied during therapy based on physiological parameters from the patient's respiratory gases or other physiological parameters from other physiological sensors.

The illustrated graphical example is just one means by which the measuring head 500 or an associated display can provide a clinician with instructions or feedback for manual ventilation therapy. Animated graphical representations of compression can be used, such as an animated graphic of a hand squeezing and releasing a bag, an icon of lungs inflating and deflating, or the like. Auditory representations can be used such as verbal instructions or a sound that increases or decreases in pitch or volume. These examples are meant to illustrate and not to limit the manual ventilation instruction capabilities of the systems discussed herein.

Figure 5C:
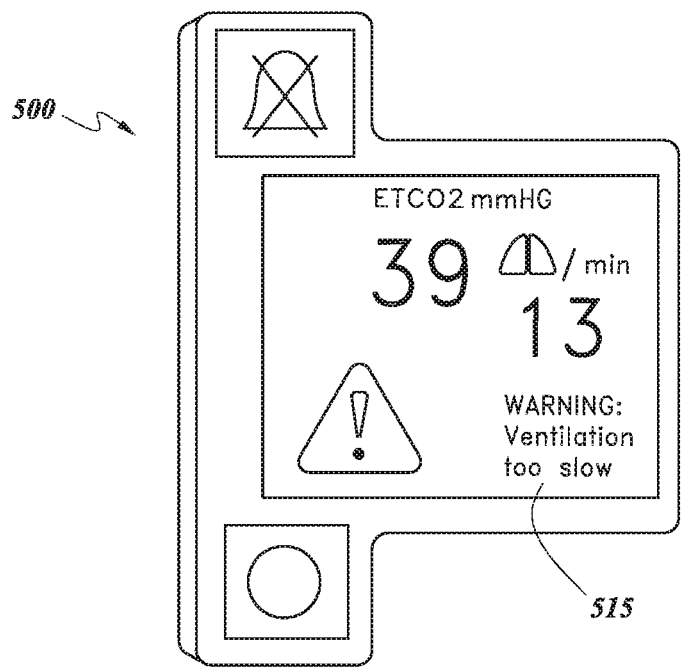
Figure 5D:
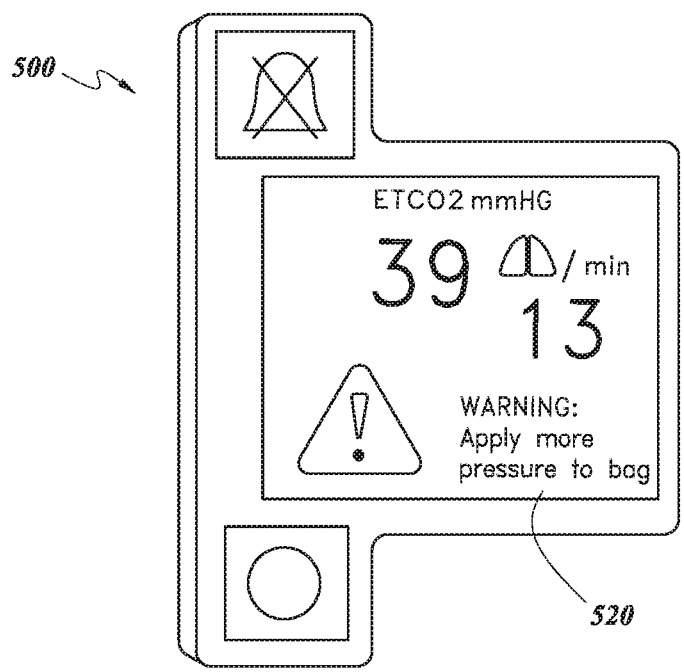

As illustrated in FIG. 5C and FIG. 5D, the measuring head 500 display can be used to provide feedback such as a warning to a care provider. One example of a warning can be an indication that ventilation is too slow 515, indicating that the care provider should increase a rate of compressing a resuscitation bag. Another example of a warning can be an indication 520 to apply more pressure to a resuscitation bag. Other warnings and indications are possible in other embodiments.

Figure 6:
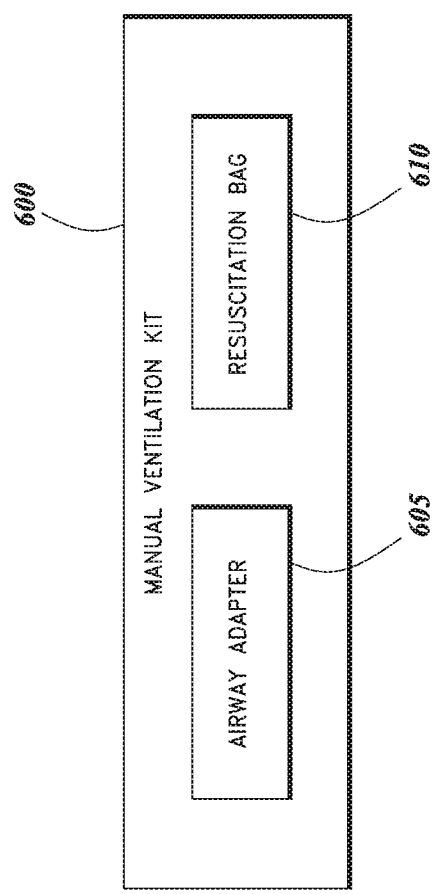
FIG. 6 illustrates an embodiment of a manual ventilation kit.

FIG. 6 illustrates an embodiment of a manual ventilation kit 600. In the illustrated embodiment, the kit 600 can include an airway adapter 605 and a resuscitation bag 610. In other embodiments the kit 600 can include multiple airway adapters and multiple resuscitation bags. The airway adapter 605 and resuscitation bag 610 can be matched according to patient age or size, for example an adult airway adapter and an adult resuscitation bag. Another example of a kit can include an infant airway adapter and an infant resuscitation bag. The kit can be packaged so as to keep the contents sterile. One or both of the airway adapter 605 and resuscitation bag 610 can include an information element as described above.

II. Example Physiological Monitoring Processes

Figure 7:
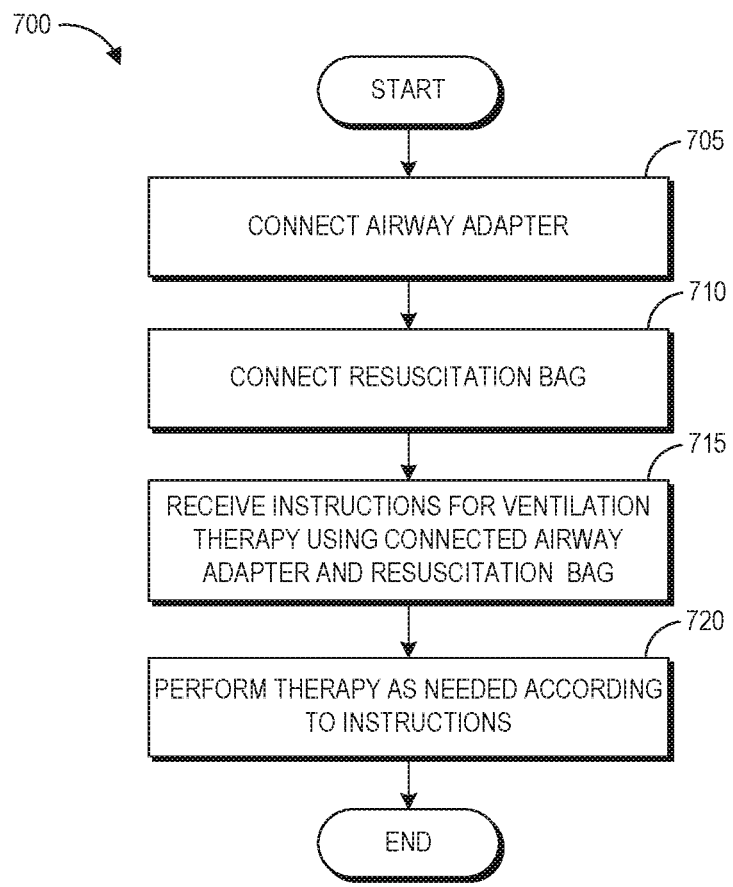
FIG. 7 illustrates an embodiment of a manual ventilation process.

FIG. 7 illustrates an embodiment of a manual ventilation process 700. The process 700 can be implemented using systems and components as are described above with respect to FIG. 1A through FIG. 6, or by any manual ventilation system having the component-recognizing and instruction-generating capabilities discussed herein.

The process 700 begins at block 705 when a clinician or other care provider connects a disposable airway adapter to a reusable respiratory gas measurement device. This can cause electrical or wireless connection of an information element located on the airway adapter with a processor of the measurement device, as discussed above. The measurement device can determine whether the airway adapter has an information element and, if so, whether data on the information element identifies a size, type, or manufacturer of the airway adapter.

At block 710, the clinician connects a resuscitation bag to the measurement device. This can cause electrical or wireless connection of an information element located on the resuscitation bag with a processor of the measurement device, as discussed above. The measurement device can read the information element as discussed above.

At block 715, the clinician can receive instructions for ventilation therapy performed using the connected airway adapter and resuscitation bag. The instructions can include one or more of assembly instructions, patient placement instructions, or therapy instructions. The therapy instructions can include one or both of compression rate and compression depth for the resuscitation bag. As discussed above, the clinician can receive the instructions on the measurement device or a connected display such as the clinician's smartphone.

At block 720, the clinician can perform therapy as needed according to the instructions. In some embodiments, the instructions can be updated based on physiological parameters of the patient as determined by the measurement device.

Figure 8:
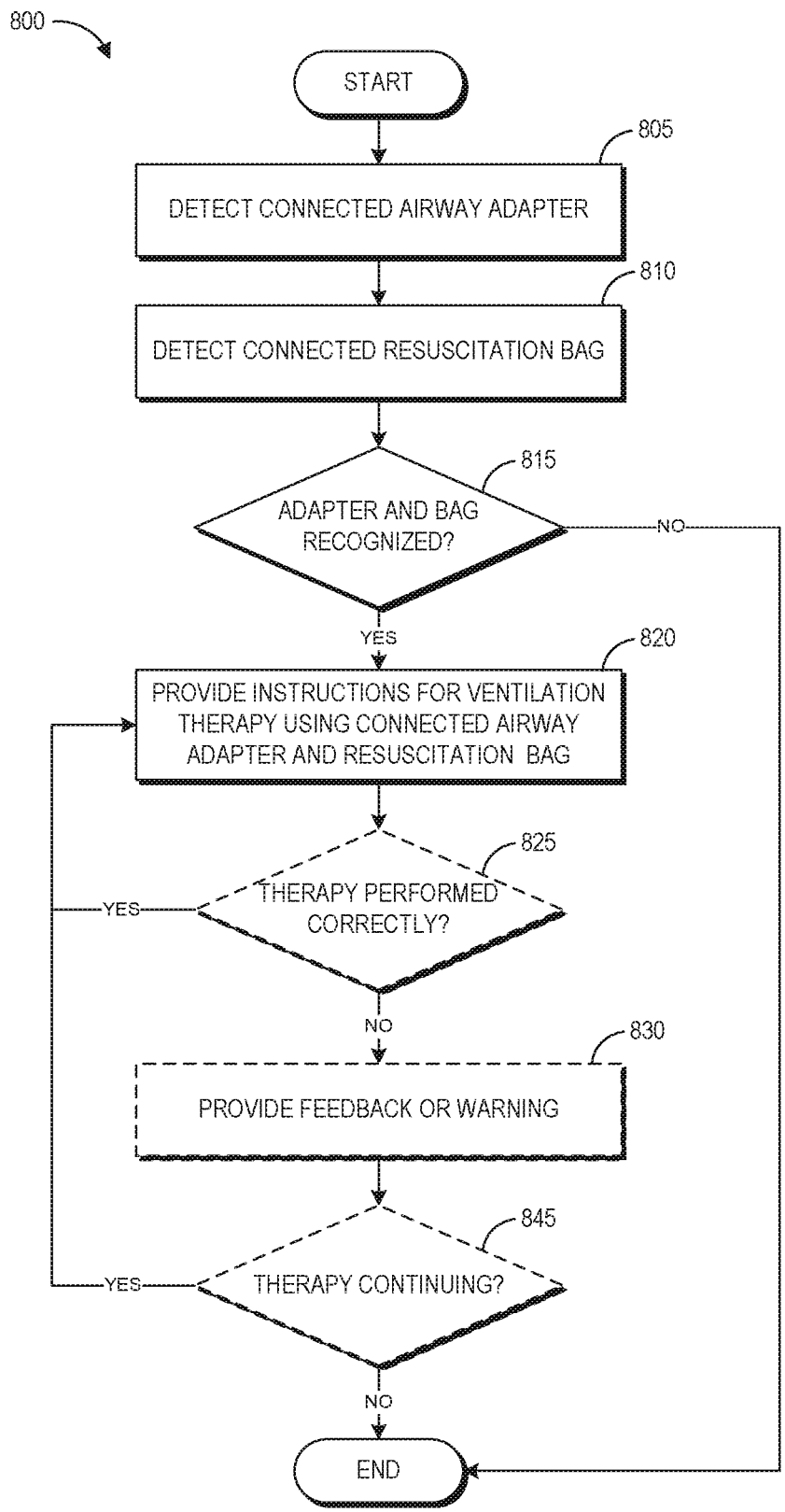
FIG. 8 illustrates an embodiment of a process for providing ventilation instructions.

FIG. 8 illustrates an embodiment of a process 800 for providing active feedback ventilation instructions. The process 800 can be implemented using systems and components as are described above with respect to FIG. 1A through FIG. 6, or by any manual ventilation system having the component-recognizing and instruction-generating capabilities discussed herein.

The process 800 begins at block 805 when a respiratory gas measurement device detects a connected airway adapter. A measurement device can be the measurement head 105 of FIGS. 1A-1B in some embodiments. The airway adapter can be detected using an information element, pressure sensing, clinician input, or other known means. The measurement device can detect the airway adapter in preferred embodiments using electrical or wireless connection of an information element located on the airway adapter with a processor of the measurement device, as discussed above. The measurement device can determine whether the airway adapter has an information element in some embodiments or whether the airway adapter is an unknown adapter with no information element.

At block 810, the respiratory gas measurement device detects a connected resuscitation bag. The resuscitation bag can be detected using an information element, pressure sensing, clinician input, or other known means. The measurement device can detect the resuscitation bag in preferred embodiments using electrical or wireless connection of an information element located on the resuscitation bag with a processor of the measurement device, as discussed above. The measurement device can determine whether the resuscitation bag has an information element in some embodiments or whether the resuscitation bag is an unknown bag with no information element.

At decision block 815, the measurement device can determine whether the adapter and bag are recognized. A recognized adapter or bag in one example can be an adapter or bag associated with instructions. The instructions can be stored locally on the measurement device in some embodiments, or in other embodiments can be stored in another location such as on an information element read by the measurement device or on a server accessed by the measurement device through a network. In one embodiment, if one or both of the adapter and bag are not recognized, then the process 800 can end. In another embodiment, only if both of the adapter and bag are not recognized will the process 800 end.

If one or both of the adapter and bag are recognized, then the process transitions to block 820. At block 820, the measurement device provides instructions for ventilation therapy performed using the connected airway adapter and resuscitation bag. The instructions can include one or more of assembly instructions, patient placement instructions, or therapy instructions. The therapy instructions can include one or both of compression rate and compression depth for the resuscitation bag, and can be delivered graphically or through auditory devices. As discussed above, the clinician can receive the instructions on the measurement device or a connected display such as the clinician's smartphone.

Optionally, at block 825, the measurement device can determine whether the ventilation therapy is being performed correctly. For example, the measurement device can determine the concentration of a desired substance (such as carbon dioxide, oxygen, etc.), in exhaled gases of the patient. The concentration can be compared to a range or threshold indicating that adequate ventilation is being provided to the patient. If therapy is being performed correctly, then the process 800 can loop back to block 820 to continue providing instructions for ventilation to the clinician. The process 800 can periodically or continuously perform the determination of block 825.

If, at block 825, the measurement device determines that ventilation therapy is not being performed correctly, then the process 800 transitions to optional block 830. Optionally, at block 830, the measurement device can provide feedback or a warning to indicate that the patient is receiving inadequate ventilation. For example, the feedback can include a change to the instructions, such as an increase or decrease in compression rate. The feedback can also include textual or spoken instructions regarding changes in therapy technique. As another example, a warning can be issued indicating that ventilation is too fast or too slow.

The process 800 can then transition to optional block 845 to determine whether therapy is on-going or has ceased. This can be determined based on clinician input, prompting the clinician to indicate whether therapy is continuing, or by monitoring patient physiological parameters. If therapy is not continuing then the process 800 can end. If therapy is continuing then the process 800 can loop back to block 820 to continue providing instructions for ventilation to the clinician. In some embodiments, block 845 can be omitted and the process 800 can continue as long as the measurement device is powered on and/or connected to an airway adapter and ventilation bag.

III. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, any of the signal processing algorithms described herein may be implemented in analog circuitry. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A physiological monitoring system comprising:
a respiratory gas measurement device including a processing board;
an airway adapter configured to connect to the respiratory gas measurement device and to direct exhaled respiratory gases of a patient to the respiratory gas measurement device, the airway adapter comprising a first information element configured to store adapter data representing information regarding at least one characteristic of the airway adapter; and
a resuscitation bag configured to connect to the airway adapter and to provide positive pressure ventilation to the patient, the resuscitation bag comprising a second information element configured to store bag data representing information regarding at least one characteristic of the resuscitation bag,
wherein the processing board is configured to:
generate instructions for manual ventilation based on one or both of the adapter data and the bag data, wherein the instructions include an animated sequence and wherein a timing of the animated sequence is configured to vary to provide visual feedback, and
cause output of the instructions for manual ventilation to a user,
wherein the processing board communicates with the first information element to read the adapter data, and
wherein the processing board communicates with the second information element to read the bag data.

2. The physiological monitoring system of claim 1, wherein the adapter data includes one or more of a size, type, manufacturer, or usage of the airway adapter.

3. The physiological monitoring system of claim 1, wherein the bag data includes one or more of a size, volume, manufacturer, or usage of the resuscitation bag.

4. The physiological monitoring system of claim 1, wherein the first information element and the second information element each comprise one or more of a transistor network, memory chip, EPROM, multi-contact single wire memory device, resistor, capacitor, microchip, RAM, ROM, RFID tag, NFC chip, and barcode.

5. The physiological monitoring system of claim 1, wherein the processing board is configured to determine a compression depth for compression of the resuscitation bag based at least partly on the bag data, wherein the instructions for manual ventilation include the compression depth.

6. The physiological monitoring system of claim 1, wherein the processing board is configured to determine age-specific ventilation instructions based at least partly on the adapter data, wherein the instructions for manual ventilation include the age-specific ventilation instructions.

7. The physiological monitoring system of claim 1, wherein the processing board is configured to determine a compression rate for compression of the resuscitation bag based at least partly on the bag data, wherein the instructions for manual ventilation include the compression rate.

8. The physiological monitoring system of claim 7, wherein the respiratory gas measurement device comprises a display configured to display the instructions for manual ventilation.

9. The physiological monitoring system of claim 1, wherein the respiratory gas measurement device is configured to monitor one or more respiratory parameters of the patient, and wherein the processing board is configured to update the instructions for manual ventilation based at least partly on the one or more respiratory parameters of the patient.

10. The physiological monitoring system of claim 9, wherein the instructions for manual ventilation after the update include feedback on effectiveness of compressions of the resuscitation bag.

11. The physiological monitoring system of claim 9, wherein the instructions for manual ventilation include a graphical representation of compression rate and compression depth for compression of the resuscitation bag, and wherein the processing board is configured to communicate the instructions to a display.

12. The physiological monitoring system of claim 9, wherein the instructions for manual ventilation include an auditory signal for guiding compression rate and compression depth for compression of the resuscitation bag.

13. A physiological monitoring method comprising:
providing a respiratory gas measurement device including a processing board;
providing an airway adapter configured to connect to the respiratory gas measurement device and to direct exhaled respiratory gases of a patient to the respiratory gas measurement device, the airway adapter comprising a first information element configured to store adapter data representing information regarding at least one characteristic of the airway adapter;
providing a resuscitation bag configured to connect to the airway adapter and to provide positive pressure ventilation to the patient, the resuscitation bag comprising a second information element configured to store bag data representing information regarding at least one characteristic of the resuscitation bag;
communicating, via the processing board, with the first information element to read the adapter data;
communicating, via the processing board, with the second information element to read the bag data;

generating, via the processing board, manual ventilation instructions based on one or both of the adapter data and the bag data, wherein the instructions include an animated sequence and wherein a timing of the animated sequence is configured to vary to provide visual feedback; and providing the manual ventilation instructions to a user.

14. The physiological monitoring method of claim 13, wherein the respiratory gas measurement device is configured to monitor one or more respiratory parameters of the patient, the method further comprising:

performing manual ventilation of the patient according to the manual ventilation instructions; and updating, via the processing board, the manual ventilation instructions based at least partly on the one or more respiratory parameters of the patient.

15. The physiological monitoring method of claim 14, wherein the manual ventilation instructions after the update include feedback on effectiveness of compressions of the resuscitation bag.

16. The physiological monitoring method of claim 13, wherein the manual ventilation instructions include a graphical representation of compression rate and compression depth for compression of the resuscitation bag, the method further comprising communicating the manual ventilation instructions from the processing board to a display.

17. The physiological monitoring method of claim 13, wherein the manual ventilation instructions include an auditory signal for guiding compression rate and compression depth for compression of the resuscitation bag.

18. The physiological monitoring method of claim 13, wherein the adapter data includes one or more of a size, type, manufacturer, or usage of the airway adapter, the method further comprising determining age-specific ventilation instructions based at least partly on the adapter data, wherein the manual ventilation instructions include the age-specific ventilation instructions.

19. The physiological monitoring method of claim 13, wherein the bag data includes one or more of a size, volume, manufacturer, or usage of the resuscitation bag, the method further comprising determining one or both of a compression rate and a compression depth for compression of the resuscitation bag based at least partly on the bag data, wherein the manual ventilation instructions include the compression rate.

\* \* \* \* \*